(12) United States Patent
Nishino et al.

(10) Patent No.: US 6,808,603 B1
(45) Date of Patent: Oct. 26, 2004

(54) METHOD FOR SYNTHESIZING ABSOLUTE ASYMMETRY

(75) Inventors: Hideo Nishino, Toyonaka (JP); Asao Nakamura, Toyonaka (JP); Yoshihisa Inoue, Toyonaka (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/070,048

(22) PCT Filed: Mar. 15, 2000

(86) PCT No.: PCT/JP00/01561

§ 371 (c)(1),
(2), (4) Date: Feb. 22, 2002

(87) PCT Pub. No.: WO01/14287

PCT Pub. Date: Mar. 1, 2001

(30) Foreign Application Priority Data

Aug. 23, 1999 (JP) .......................................... 11-236171

(51) Int. Cl.⁷ ................................................ C07C 7/00
(52) U.S. Cl. ................................................ 204/157.15
(58) Field of Search .................................. 204/157.15

(56) References Cited

FOREIGN PATENT DOCUMENTS

| EP | 0 285 175 | 10/1988 |
|---|---|---|
| EP | 0 658 373 | 6/1995 |
| JP | 57-147577 | 9/1982 |
| JP | 09-077691 | 3/1997 |
| JP | 2000-86586 | 3/2000 |

OTHER PUBLICATIONS

Nishino et al., Absolute Asymmetric Synthesis of Norbornadiene and Quadricyclane Derivatives With Circularly Polarized Light First Reversible Asymmetric Photoisomerization Between Norbornadienes and Quadricyclanes With Circularly Polarized Light.*

Proceedings II of 1999 76th National Meeting of Chemical Society of Japan, Mar. 15, 1999, translation, pp. 1–3.*

Salam et al., "On Enantiomeric Excesses Obtained From Racemic Mixtures by Using Circularly Polarized Pulsed Lasers of Varying Durations", Chemical Physics, vol. 228 (no month, 1998), pp. 115–129.*

Tran, C.D., et al., "Stereoselective Energy Transfer Induced by Circularly Polarized Light," Study Phys. Theory Chem. vol. 7 p. 53–66, 1979. no month.

Miesen, F.W.A.M., et al., "Synthesis of Optically Pure 3–('nπ*)–(1S.6R)–Bicyclo[4.4.0]decane–3.8 dione, a Molecule Which is Chiral in the Excited State Only," J.Am. Chem. Soc., vol. 116, No. 12, p. 5129–5133, 1994. no month.

(List continued on next page.)

*Primary Examiner*—Edna Wong
(74) *Attorney, Agent, or Firm*—Knobbe, Martens Olson & Bear LLP

(57) ABSTRACT

The present invention provides a novel method for absolute asymmetric synthesis by irradiation with circularly polarized light,
which comprises providing a photochemically reversible reaction system in which the starting material is a mixture of enantiomers or diastereomers not photochemically or thermally converted into each other; and
irradiating the reaction system with right- or left-circularly polarized light to excite the starting material alone or both of the starting material and the product, thereby concentrating one of the enantiomers or diastereomers in the starting material and one of the enantiomers or diastereomers in the product that corresponds to the enantiomer or diastereomer not concentrated in the starting material.

11 Claims, 14 Drawing Sheets

OTHER PUBLICATIONS

Inoue, Y., et al., "Hikari de Fusei Gousei ni semaru," Sakigake Kenkyu 21 Kenkyu Houkokuai, Hikari to Busshitsu Kouen Youshishuu 1994, p. 42–48, 1995. no month.

Salam, A., et al., "On enantiomeric excess obtained from racemic mixtures by using circularly polarized pulsed lasers of varying durations," Chem.Phys. vol. 228, No.1, p. 115–128, 1998. no month.

Bumham, K.S., et al., "A Search for Chiral Photochromic Optical Triggers for Liquid Crystals: Photoracemization of 1, 1–Binaphthylpyran through a Transient Biaryl Quinone Methide Intermediate," J. Am.Chem.Soc., vol. 120, No. 48. p. 12619–12625, 1998. no month.

Inoue, Y., et al., "Pressure and Temperature control of Product Chirality in Asymmetric Photochemistry Enantiodifferentiating Photoisomerization of Cyclooctene Sensititzed by Chiral Benzenepolycarboxlates," J.Am.Chem.Soc., vol. 120, No. 41, p. 10687–10696. 1998.

Nishino, H. et al., "First Reversible Asymmetric Photoisomerization with Circularly Polarized Light Absolute Asymmetric Synthsis of Norbomadiane and Quadricyclane," Proceedings II of 1999 76th National Meeting of Chemical Society of Japan, p. 1157, 1C741, Mar. 15, 1999.

Inoue Y, et al. "Absolute Asymmetric Syntheses of Norbomadiene and Quadricyclane Derivatives with Circularly Polarized Light First Reversible Asymmetric Photoisomerization between Norbornadienes and Quadricyclanes with Circularly Polarized Light" and its translation, no date.

Nishino, H., et al. "Absolute Asymmetric Syntheses of Norbomadiene and Quadricyclane Derivatives with Circularly with Circularly Polarized Light: First Reversible Asymmetric Photoisomerization between Norbomadianes and Quadricyclanes Polarized Light," Proceedings II of of 1999 76th National meeting of Chemical Society of Japan, p. 1157, 1C741, Mar. 15, 1999 (translation).

* cited by examiner-

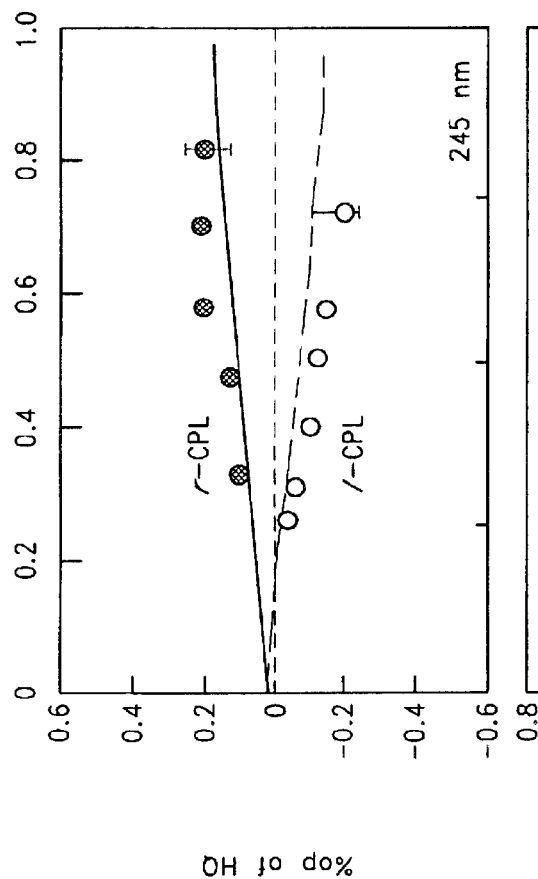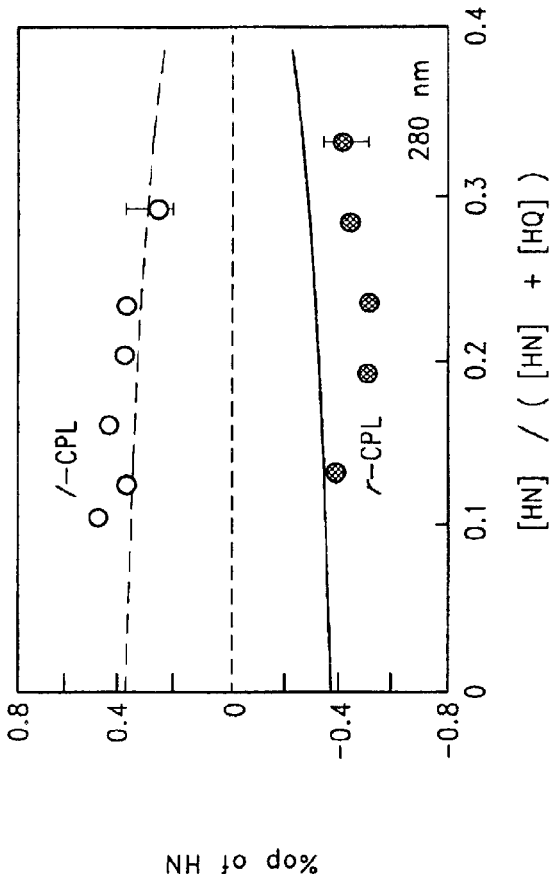
FIG. 13A
FIG. 13B

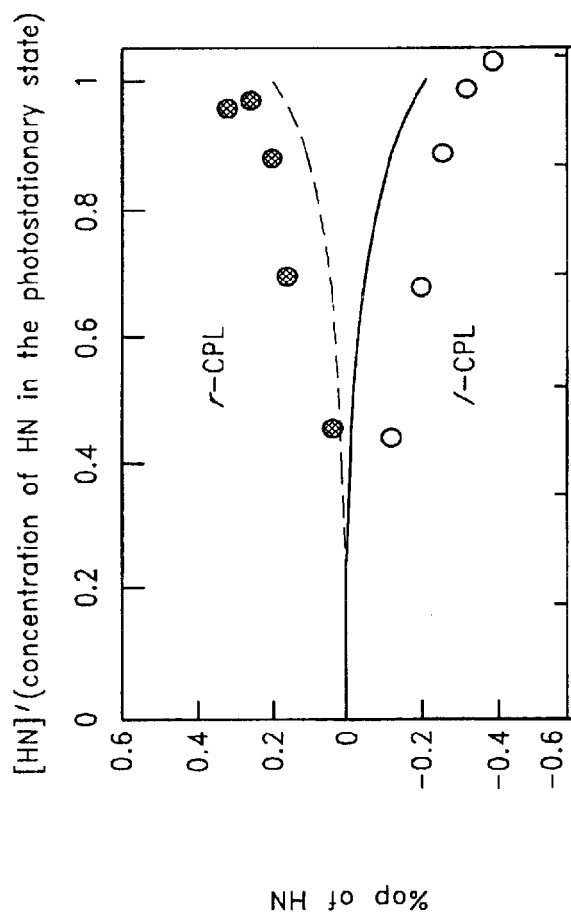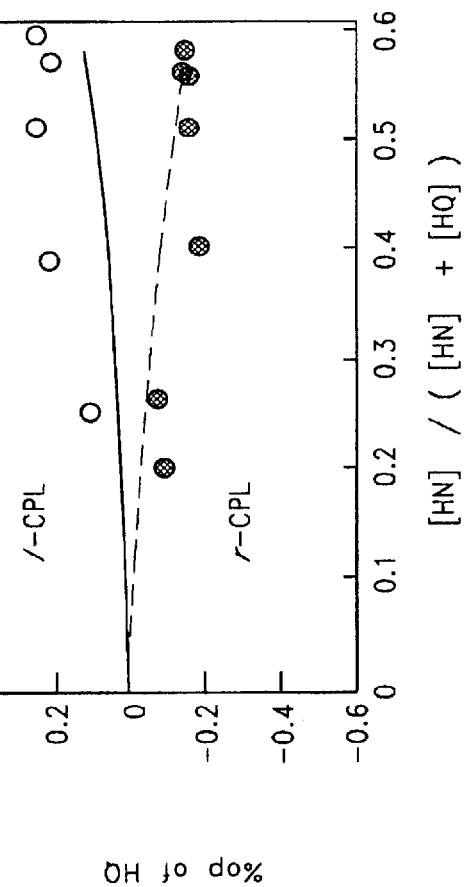
FIG. 14A
FIG. 14B

METHOD FOR SYNTHESIZING ABSOLUTE ASYMMETRY

This application is the U.S. National Phase under 35 U.S.C. §371 of International Application PCT/JP00/01561, filed Mar. 15, 2000, which claims priority to Japanese Patent Application No. 11/236171, filed Aug. 23, 1999. The International Application was published under PCT Article 21(2) in a language other than English.

TECHNICAL FIELD

The present invention relates to a method for absolute asymmetric synthesis. More specifically, the invention relates to a novel method for absolute asymmetric synthesis, which enables concentration of one of the enantiomers or diastereomers in the starting material and one of the enantiomers or diastereomers in the product, in a reaction system in which the enantiomers or diastereomers are not converted into each other chemically or thermally.

BACKGROUND ART

Asymmetric synthesis plays an important role in the preparation of various optically active chemicals, such as pharmaceuticals, agricultural chemicals, perfumes, cosmetics, and intermediates thereof. In the second half of the nineteenth century, the usefulness of right- and left-circularly polarized light (r-CPL and l-CPL) was confirmed by van't Hoff. Since then, there have been many attempts to produce optically active chemicals using circularly polarized light (CPL).

Such synthesis of optically active chemicals using CPL is one type of "absolute asymmetric synthesis" (AAS). That is, asymmetric induction is realized by preferential excitation of one of the enantiomers by means of irradiation with right- or left-circularly polarized light. The anisotropic factor, also known as "g", is considered to determine the degree of selective excitation. The anisotropic factor g was defined by Kuhn as the difference between optical isomers in molar absorption coefficient for r- or l-CPL at a certain wavelength as follows:

$$g=(\epsilon_l-\epsilon_r)/\epsilon=\Delta\epsilon/\epsilon \quad (1)$$

in which $\epsilon=(\epsilon_l-\epsilon_r)/2$ and $0 \leq g < 2$ (Trans. Faraday. Soc. 1930, 293–309; Z. Phys. Chem., B. Abt. 1930, 7, 292–310).

Absolute asymmetric synthesis (AAS) is classified into three categories: (a) asymmetric photolysis, (b) photochemical deracemization and (c) photochemical asymmetric fixation.

In asymmetric photolysis, the two enantiomers in the starting material are photochemically decomposed in different extents depending on the degree of their selective excitation by irradiation with r- and l-CPL at a certain wavelength. Scheme (1 shows this asymmetric photolysis.

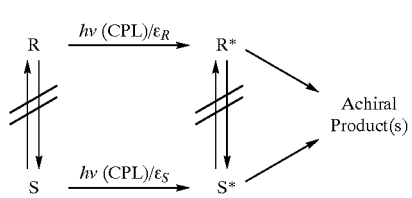

[1]

In place of $\epsilon_l$ and $\epsilon_r$, $\epsilon_R$ and $\epsilon_S$ are used herein. $\epsilon_R$ and $\epsilon_S$ represent molar absorption coefficients of the two enantiomers for r-CPL or l-CPL, respectively. The enantiomer less excited by r- or l-CPL remains in the starting material and the optical purity is increased, whereas the other enantiomer decomposes. In this type of absolute asymmetric synthesis, the photochemical process is irreversible. There are many reports on such asymmetric photolysis. Representative examples are a report on photolysis of camphor (Z. Phys. Chem., Abt. B, 1930, 292–310) and a report on photolysis of trans-bicyclo[4,3,2]nonan-8-one (J. Chem. Soc., Chem. Commun. 1978, 983–4).

Scheme [2] shows a photochemical deracemization process. As shown in Scheme [2], the total concentration of the enantiomers does not change during the photoreaction. Preferential excitation of one of the enantiomers over the other shifts the photochemical equilibrium, and the enantiomer ratio is fixed upon termination of irradiation. However, except for inorganic compounds (Mol. Photochem. 1969, 1, 271; Chem. Commun. 1996, 2627–2628), there are only a few reports of photochemical deracemization. Organic compounds, which exclusively undergo photoderacemization, have been rarely reported. Actually, it appears that side reactions always occur when organic compounds are photochemically deracemized.

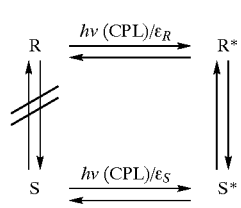

[2]

The photochemical process of asymmetric fixation resembles asymmetric photolysis. In the process, the starting material undergoes thermal racemization and as shown in Scheme [3], an enantiomer-selective photoreaction is induced by irradiation with r- or l-CPL and thereafter an optically active product is obtained. The R/S ratio of the product is equal to the molar absorption coefficient ratio, $\epsilon_R/\epsilon_S$. There are not many examples of such photochemical asymmetric fixation. This type of photochemical asymmetric fixation includes, for example, oxidative photocyclization of 1-(2-benzo[c]phenanthryl)-2-phenylethylene to hexahelicene via dihydrohericene (J. Am. Chem. Soc. 1971, 93, 2553; J. Am. Chem. Soc. 1973, 95, 527–32).

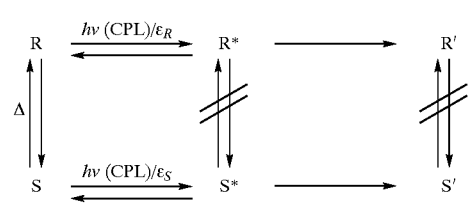

[3]

The reversible absolute asymmetric synthesis of 1,1'-binaphthyl pyran recently proposed by G. B. Schuster, et al. is a variation of photochemical deracemization (J. Am. Chem. Soc. 1998, 120, 12619–12625).

As shown above, conventional methods for absolute asymmetric synthesis using circularly polarized light are methods for obtaining, in the starting material, an excess amount of one enantiomer relative to the other primarily by utilizing preferential decomposition or shifting the enantiomer ratio by means of irradiation with circularly polarized light.

Under the circumstances described above, the present invention was made. The present invention focuses on the reaction product to which none of the conventional researchers have paid attention. An object of the present invention is to provide a novel method for absolute asymmetric synthesis, which enables concentration of one of the enantiomers or diastereomers in the starting material and one of the enantiomers or diastereomers in the product, in a reaction system in which the enantiomers or diastereomers (i.e., R-isomer and S-isomer relative to one asymmetric carbon) are not chemically or thermally converted into each other.

DISCLOSURE OF INVENTION

To achieve the above object, the present invention provides the following inventions:

First, the present invention provides a method for synthesizing absolute asymmetry which comprises: providing a photochemically reversible reaction system in which the starting material is a mixture of enantiomers or diastereomers not photochemically or thermally converted into each other; and irradiating the reaction system with right- or left-circularly polarized light to excite the starting material alone or both the starting material and the product, thereby concentrating one of the enantiomers or diastereomers in the starting material and one of the enantiomers or diastereomers in the product that corresponds to the enantiomer or diastereomer not concentrated in the starting material.

Secondly, the present invention provides the above method in which the starting material and the product are mixtures of enantiomers and only the starting material is excited, the concentration of one of the enantiomers in the starting material and one of the enantiomers in the product being controlled by adjusting the anisotropic factor g, which indicates the degree of selective excitation by right- and left-circularly polarized light.

Thirdly, the present invention provides the above method in which the starting material and the product are mixtures of enantiomers and both the starting material and the product are excited, the concentration of one of the enantiomers in the starting material and one of the enantiomers in the product being controlled by adjusting at least one of the following:

the value of anisotropic factor g which indicates the degree of selective excitation by right- and left-circularly polarized light;

plus or minus sign of g; and

K indicating the photochemical equilibrium of the reaction.

BRIEF DESCRIPTION OF DRAWINGS

FIGS. 13(a) and 13(b) shows a simulated calculation and experimental data of HQ excited by CPL irradiation (245 nm). FIG. 13(a) shows the relationship between the optical purity (% op) of the starting material (HQ) and conversion. FIG. 13(b) shows the relationship between the optical purity (% op) of the product (HN) and conversion.

FIGS. 14(a) and 14(b) shows a simulated calculation and experimental data of RN excited by CPL irradiation (245 nm). FIG. 14(a) shows the relationship between the optical purity (% op) of the starting material (HN) and conversion ratio. FIG. 14(b) shows the relationship between the optical purity (% op) of the product (HQ) and conversion.

BEST MODE FOR CARRYING OUT THE INVENTION

Figure 1A:
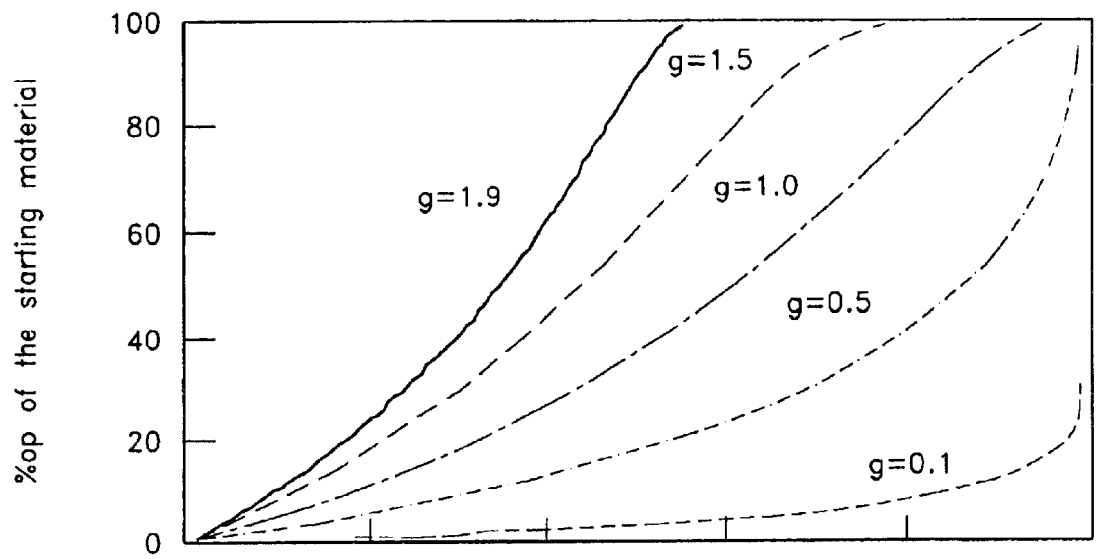
FIG. 1(a) shows the relationship between the optical purity (% op) of the starting material and conversion by CPL irradiation, corresponding to different values of g for the starting material, in a reaction system of class (A)

The present invention has the features described above. Preferred modes for carrying out the invention will be described below.

The method for synthesizing absolute asymmetry according to the first embodiment of the invention comprises:

providing a photochemically reversible reaction system in which the starting material is a mixture of enantiomers or diastereomers not photochemically or thermally converted into each other; and irradiating the reaction system with right- or left-circularly polarized light to excite the starting material alone or both of the starting material and the product, thereby concentrating one of the enantiomers or diastereomers in the starting material and one of the enantiomers or diastereomers in the product (or achieving further concentration of one of the enantiomers or diastereomers in the starting material and/or the product, if already concentrated). The photochemically reversible system includes a reaction reversible by irradiation with the same kind of light at the same wavelength, and a reaction reversible by irradiation with a different kind of light or with the same kind of light but at a different wavelength.

The mixture of enantiomers includes a racemic mixture that is an equivalent mixture. Diastereomers can also be used in the invention because they can be considered as an R-isomer or an S-isomer, relative to one asymmetric carbon in the molecular structure, for example, in the case of no interaction between asymmetric centers.

Optically reversible reaction systems can be classified into two classes shown in Scheme [4].

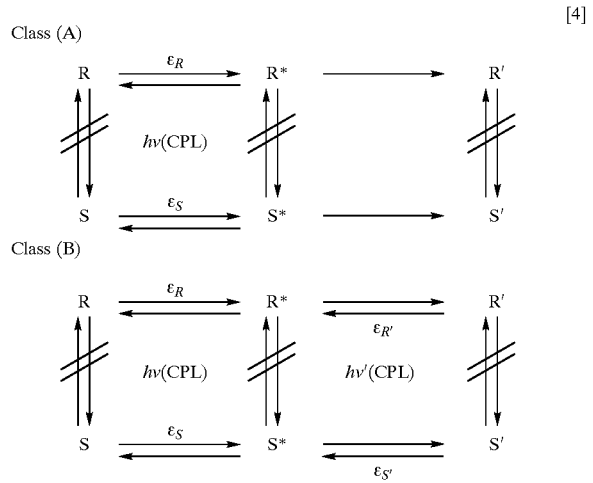

Class (A)

Class (B)

[4]

In class (A), only the starting material is excited with circularly polarized light (CPL) and the product is not excited. In class (B), both the starting material and the product are excited.

A representative example of the starting material-product reaction system of the present invention is a norbornadiene derivative-quadricyclane derivative system.

However, the kinds of starting material and product in the absolute asymmetric synthesis method of the present invention are not specifically limited.

Norbornadiene and quadricyclane have been investigated in detail because photoisomerization from norbornadiene to quadricyclane has potential for solar energy storage. Quadricyclane is a thermally stable compound and classified structurally as a highly distorted cyclobutane derivative. Quadricyclane can be photochemically synthesized via [2+2] intramolecular cycloaddition of photochemically excited norbornadiene. It is also possible to produce norbornadiene by the reverse reaction, i.e., photochemical or thermal reaction of quadricyclane.

The photoisomerization between chiral norbornadiene derivatives and quadricyclane derivatives formed by introduction of asymmetric substituents is a reaction system in which enantiomers or diastereomers are not photochemically or thermally converted into each other. This photoisomerization is an example of the absolute asymmetric synthesis method of the invention which enables concentration of one of the enantiomers or diastereomers in the starting material and one of the enantiomers or diastereomers in the product by irradiation with circularly polarized light (CPL).

Interestingly, it is not widely known that norbornadiene and quadricyclane have a prochiral structure. There are only a few reports describing the optical properties of chiral norbornadiene derivatives. As far as the present inventors know, there has been no report on the optical properties of chiral quadricyclane derivatives. In addition, no systematic investigation has been carried out on photochemical conversion between chiral norbornadiene and quadricyclane. Therefore, the stereochemical consequences of the photocyclization have yet to be clarified.

Of course, the present invention is not limited to the norbornadiene derivatives-quadricyclane derivatives system.

As mentioned above, in various starting material-product reaction systems, the method of the present invention enables concentration of one of the enantiomers or diastereomers in the starting material and one of the enantiomers or diastereomers in the product.

In class (A) and class (B) shown in Scheme [4], the present invention enables efficient concentration of one of the enantiomers in the starting material and one of the enantiomers in the product, in a highly controlled manner.

Classes (A) and (B) will be described in order below.

Class (A)

In class (A), as described in the second embodiment of the invention, the starting material and the product are mixtures of enantiomers and only the starting material is excited. One of the enantiomers in the starting material and one of the enantiomers in the product are concentrated by controlling the anisotropic factor g which indicates the degree of selective excitation of the starting material by right- and left-circularly polarized light. The g can be controlled by application of Kagan's equation shown below.

Examples of class (A) include the norbornadiene derivative-quadricyclane derivative system shown in Scheme [5].

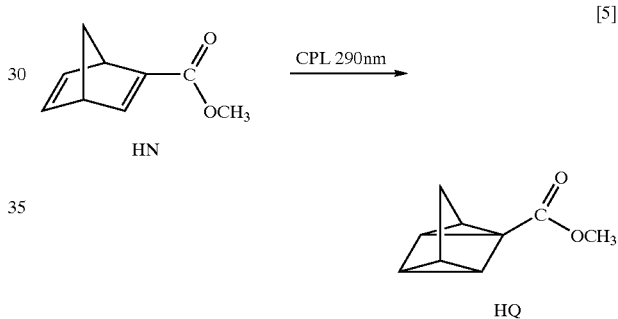

[5]

In this reaction system, when methyl bicyclo[2.2.1]hepta-2,5-diene-2-carboxylate (HN) is irradiated at 290 nm with CPL, a one-way photocyclization reaction proceeds to give methyl tetracyclo[3.2.0$^{2,7}$.0$^{4,6}$]heptane-1-carboxylate (HQ).

Theoretically, the relationship between the optical purity (% op) of the starting material and conversion (% conversion) is represented by equation (2).

$$x = 1 - (r+s) = \qquad (2)$$
$$1 - \left(\frac{1+y}{1-y}\right)^{1/g} \frac{1}{(1-y^2)^{1/2}} = 1 - \frac{1}{2}\left\{\left(\frac{1+y}{1-y}\right)^{\frac{1}{g}+\frac{1}{2}} + \left(\frac{1+y}{1-y}\right)^{\frac{1}{g}-\frac{1}{2}}\right\}$$

in which x is conversion (% conversion); y is the optical purity (% op) or % ee of the starting material; and g is the anisotropic factor of the starting material. Although equation (2) was presented by Kagan for analysis of an asymmetric photolysis process (Tetrahedron Lett. 1971, 2478–82), this equation can be applied to the starting material in class (A) in the absolute asymmetric synthesis method of the present invention.

The relationship between the optical purity (% op) or % ee of the product (y') and the conversion (% conversion)(x) is defined by equations (3) and (4), in which R' and S' represent the products obtained from enantiomers R and S in the starting material, respectively.

$$y' = \frac{([R'] - [S'])}{([R'] + [S'])} = \frac{([R]_0 - [R]) - ([S]_0 - [S])}{([R]_0 - [R]) + ([S]_0 - [S])} \quad (3)$$

$$= \frac{-([R] - [S])}{([R]_0 + [S]_0) - ([R] + [S])} = \frac{-\{([R] - [S])/([R] + [S])\}}{\{([R]_0 + [S]_0)/([R] + [S])\} - 1}$$

$$y' = \frac{y(1-x)}{x} \quad (4)$$

FIG. 1(a) shows the relationship between the optical purity (% op) of the starting material (y) and conversion (x), calculated from equation (2) with different values of g.

The results show that the optical purity (% op) of the starting material (y) reaches nearly 100% at the final stage of the reaction for all values of g except for g=0, i.e., no selective excitation with right- and left-circularly polarized light. Thus, when HN is irradiated at 290 nm with r- or l-CPL, (+)-HN or (−)-HN with an optical purity of nearly 100% can be obtained just before the end of the reaction.

Figure 1B:
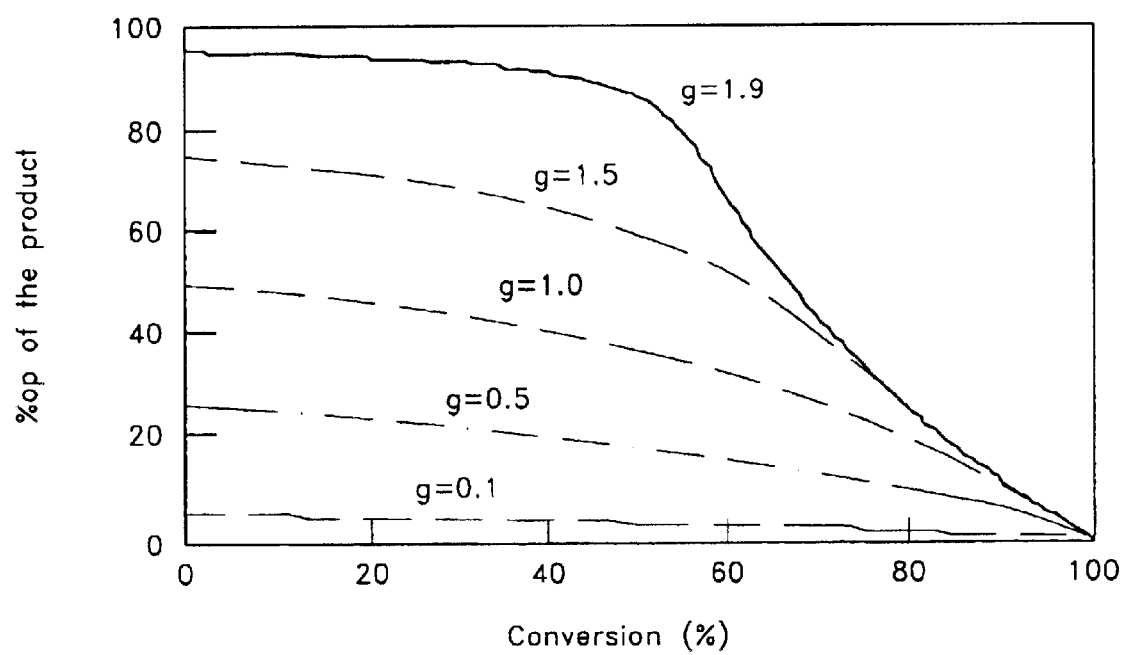
FIG. 1(b) shows the relationship between the optical purity (% op) of the product and the conversion by CPL irradiation, corresponding to different values of g for the starting material.

FIG. 1(b) shows the relationship between the optical purity (% op) of the product (y') and conversion (x), calculated from equations (2), (3) and (4) with different values of g. FIG. 1(b) shows that at the initial stage of reaction, the optical purity (% op) of the product reaches nearly (g/2)× 100%.

FIG. 1(a) and FIG. 1(b) show that, for example, when g=1 and conversion is about 50%, the optical purities (% op) of the starting material and the product are both more than 40%.

According to the second embodiment of the invention, absolute asymmetric synthesis is realized by controlling the g in the above-mentioned reaction system. Of course, the kind of light and its wavelength are selected to provide a photochemically reversible reaction system (class A).

Class (B)

In class (B), as described in the third embodiment of the invention, the starting material and the rill product are mixtures of enantiomers, respectively and both the starting material and the product are excited. One of the enantiomers in the starting material and one of the enantiomers in the product are concentrated by controlling at least one of the following:

g's of the starting material and the product;

signs of the g's; and

K indicating the photochemical equilibrium of the reaction.

The starting material and the product are photochemically reversible, and both the forward reaction and the reverse reaction can be carried out by irradiation with light. Reaction scheme [6] shows a reversible reaction in which methyl bicyclo[2.2.1]hepta-2,5-diene-2-carboxylate (HN) is photocyclized to methyl tetracyclo[3.2.0$^{2.7}$.0$^{4.6}$]heptane-1-carboxylate (HQ) by irradiation at 245 nm with CPL.

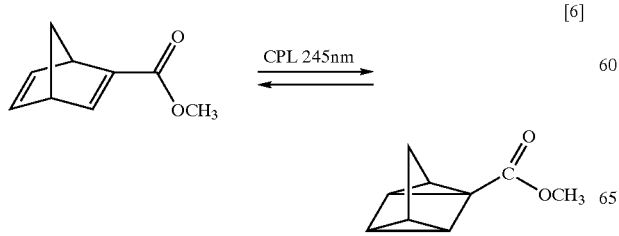

[6]

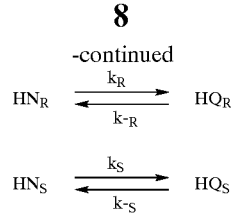

The rate equation of the photochemical reaction in this system is represented by the following:

$$\frac{dC}{dt} = -I_{ex}(1 - 10^{-Abs})\frac{\varepsilon C}{Abs}\phi. \quad (6)$$

in which C is the concentration of the reactive component; $I_{ex}$ is the intensity of absorption light ($I_0$−1); Abs is the absorbance of the sample; $\varepsilon$ is the molar absorption coefficient of the sample; $\phi$ is the reaction yield; and t is the reaction time. When Abs<1, equation (6) can be simplified to equation (7).

$$\frac{dC}{dt} = -I_{ex}\frac{\varepsilon C}{Abs}\phi \quad (7)$$

When Abs is fairly constant during the reaction, the factors other than C do not depend on t. Therefore, equation (6) can be simplified to equation (8).

$$\frac{dC}{dt} = kC \quad (8)$$

In Reaction Scheme [6], enantiomers of HQ ($HQ_R$ and $HQ_S$) are converted into HN ($HN_R$ and $HN_S$) by CPL irradiation, respectively. Abs in equations (6) and (7) is represented by the following:

$$Abs = d(\varepsilon_{QR}C_{QR} + \varepsilon_{QS}C_{QS} + \varepsilon_{NR}C_{NR} + \varepsilon_{NS}C_{NS}) \quad (9)$$

in which d is the optical path length and C is the concentration of each component (HN≡N and HQ≡Q). According to the law of conservation of mass, the following relationships exist between various concentrations (C):

$$C_O = C_Q + C_N = C_{QR} + C_{QR} + C_{NR} + C_{NS} \quad (10)$$

and $$C_O/2 = C_{QR} + C_{NR} = C_{QS} + C_{NS} \quad (11)$$

When the $\varepsilon$ values of R-isomer and S-isomer are almost equal to each other (i.e., the g is small), Abs is represented by the following:

$$Abs = d\{\varepsilon_N C_0 + (\varepsilon_Q - \varepsilon_N)C_Q\} \quad (12)$$

In this case, $$\varepsilon_Q = 1/2(\varepsilon_{QR} + \varepsilon_{QS}) \text{ and } \varepsilon_N = 1/2(\varepsilon_{NR} + \varepsilon_{NS}) \quad (13)$$

The rate equations of $HQ_R$ and $HQ_S$ in Reaction Scheme [6] are represented by the following:

$$\frac{dC_{QR}}{dt} = -k_R C_{QR} + k_{-R} C_{NR} \quad (14)$$

-continued $$\frac{dC_{QS}}{dt} = -k_S C_{QS} + k_{-S} C_{NS}$$

Therefore, the optical purities (% op) of HQ and HN, and conversion (x) are defined as follows:

$$op_Q = \frac{C_{QR} - C_{QS}}{C_{QR} + C_{QS}} \quad (15)$$

$$op_N = \frac{C_{NR} - C_{NS}}{C_{NR} + C_{NS}} = -op_Q \frac{1-x}{x} \quad (16)$$

$$x = \frac{C_N}{C_0} = \frac{C_{NR} + C_{NS}}{C_0} = \frac{C_0 - (C_{QR} + C_{QS})}{C_0} \quad (17)$$

The molar absorption coefficient of R-isomer (QR) generated by l-CPL irradiation of HQ is equal to that of S-isomer (QS) generated by r-CPL irradiation of HQ. Therefore, $g_Q$ can be rewritten as follows:

$$g_Q = 2\frac{\varepsilon^r_{QR} - \varepsilon^l_{QR}}{\varepsilon^r_{QR} + \varepsilon^l_{QR}} = 2\frac{\varepsilon^l_{QR} - \varepsilon^r_{QS}}{\varepsilon^l_{QR} + \varepsilon^r_{QS}} = 2\frac{k_R - k_S}{k_R + K_S} \quad (18)$$

The progress of the reaction expressed by equation (14) exhibits the following relationships, using parameters such as $g_Q$, $g_N$, K, L and M:

$$\frac{C_{QR}}{C_0} = \frac{1}{2}\frac{K}{K+1} + \frac{1}{2}\frac{1}{K+1} e^{\{-k_R t(1+\frac{1}{K})\}} \quad (19)$$

$$\frac{C_{QS}}{C_0} = \frac{1}{2}\frac{M}{KL+M} + \frac{1}{2}\frac{KL}{KL+M} e^{\{-k_R t(L+\frac{M}{K})\}} \quad (20)$$

K, L and M are defined as follows:

$$K = \frac{k_R + k_S}{k_{-R} + k_{-S}} \quad (21)$$

$$L = \frac{k_S}{k_R} = \frac{1 - \frac{g_Q}{2}}{1 + \frac{g_Q}{2}} \quad (22)$$

$$M = \frac{k_{-S}}{k_{-R}} = \frac{1 - \frac{g_N}{2}}{1 + \frac{g_N}{2}} \quad (23)$$

Thus the optical purities (% op) of HQ and HN, and conversion (x) can be represented by the following:

$$op_Q = \frac{(K^2 L + K - MK - L) + (KL+1)e^{\{-k_R t(1+\frac{1}{K})\}} - KL(M+1)e^{\{-k_R t(L+\frac{M}{K})\}}}{(K^2 L + K + MK + L) + (KL+1)e^{\{-k_R t(1+\frac{1}{K})\}} + KL(M+1)e^{\{-k_R t(L+\frac{M}{K})\}}} \quad (24)$$

$$op_N = -op_N \frac{1-x}{x} \quad (25)$$

$$x = 1 - \left[\frac{1}{2}\frac{K}{K+1} + \frac{1}{2}\frac{1}{K+1} e^{\{-k_R t(1+\frac{1}{K})\}} + \frac{1}{2}\frac{M}{KL+1} + \frac{1}{2}\frac{KL}{KL+1} e^{\{-k_R t(L+\frac{M}{K})\}}\right] \quad (26)$$

From the above, it is clear that absolute asymmetric synthesis can be realized in class (B) by adjusting the following:

g's of the starting material and the product;
signs of the g's for the starting material and the product;
photochemical equilibrium (K) between the starting material and the product,
thereby controlling the optical purities (% op) of the starting material and the product, and conversion (x).

Figure 2A:
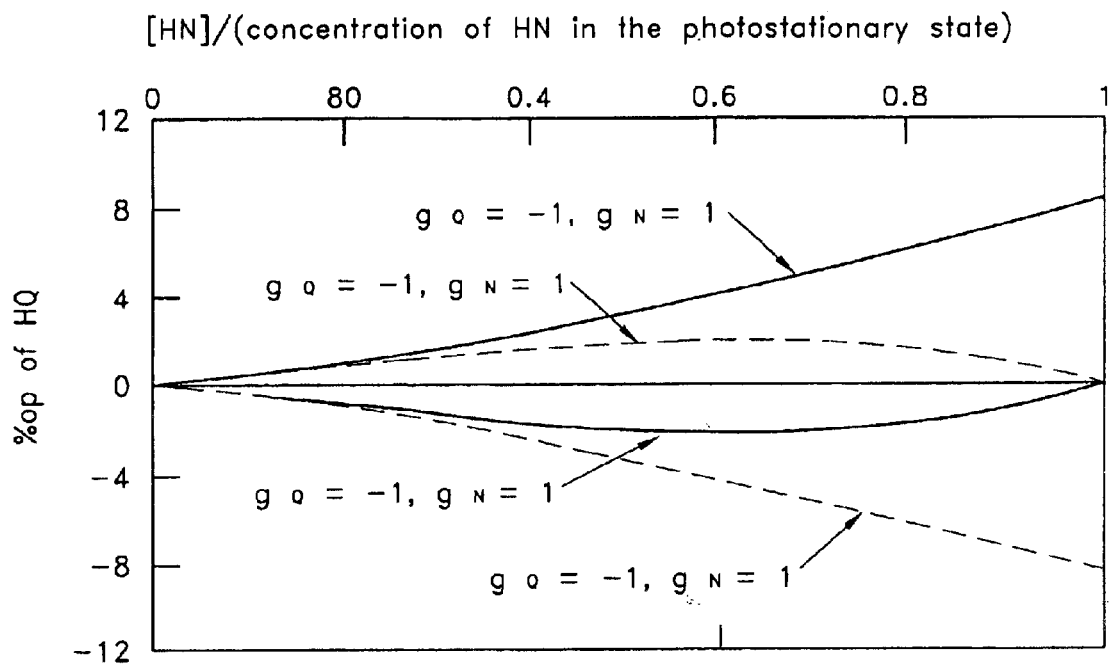
FIG. 2(a) and FIG. 2(b) show the calculated relationship between the optical purity: % op, conversion ratio, and the signs of the g's for the starting material (HQ) and the product (HN), in a reaction system of class (B).
Figure 2B:
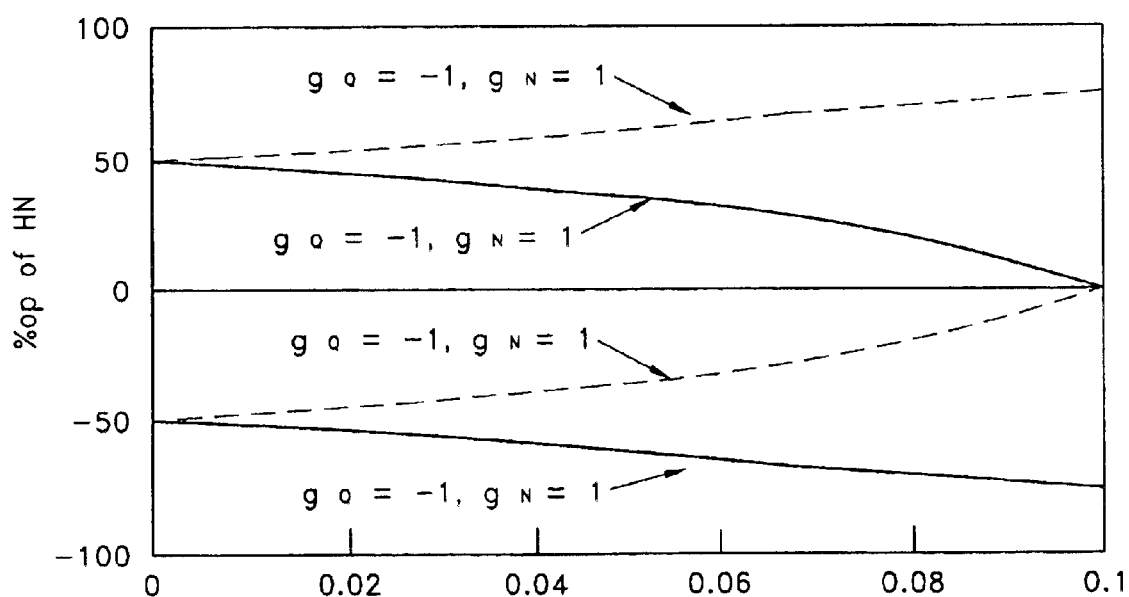

FIG. 2(a) and FIG. 2(b) illustrate the relationship among the g, the sign of g and optical purity (% op).

FIG. 2(a) and FIG. 2(b) show the optical purities (% op) of HQ and HN, calculated from equations (24), (25) and (26) with various values of $g_Q$ and $g_N$. The following two cases (I) and (II) are shown therein:

(I) $g_Q \cdot g_N > 0$; ($g_Q = 1.0$, $g_N = 1.0$: solid line) or ($g_Q = -1.0$, $g_N = -1.0$: broken line), K=0.072.

(II) $g_Q \cdot g_N < 0$; ($g_Q = 1.0$, $g_N = -1.0$: broken line) or ($g_Q = -1.0$, $g_N = 1.0$: solid line), K=0.072.

Case (I) shows $k_R > k_S$ and $k_{-R} > k_{-S}$, and case (II) $k_R > k_S$ and $k_{-R} < k_{-S}$, as obtained from equation (18).

FIG. 2(a) shows the following results:

In case (I), the optical purity (% op) of the starting material (HQ) gradually increases at the beginning of conversion but decreases in the course of the reaction. In the photostationary state (pss), the optical purity (% op) reaches zero. In case (II), the optical purity (% op) of the starting material (HQ) increases with the conversion and reaches a maximum in the photostationary state (pss).

FIG. 2(b) shows the following results:

In case (I), the optical purity (% op) of the starting material (HN) decreases from the beginning of the reaction and reaches zero in the photostationary state (pss). In case (II), the optical purity (% op) of the starting material (HN) increases as the reaction progresses, and reaches a maximum in the photostationary state (pss).

In case (II), the optical purities (% op) of the starting material (HQ) and the product (HN) increase as the reaction progresses. That is, generally, when the signs of the g's of the starting material and the product are different from each other, the optical purities (% op) of the starting material and the product increase.

In the absolute asymmetric synthesis of the present invention, sameness or difference of the signs of the g's of the starting material and the product at a CPL irradiation wave length has a large effect on the relationship between the conversion and optical purities (% op) of the starting material and the product.

Figure 3A:
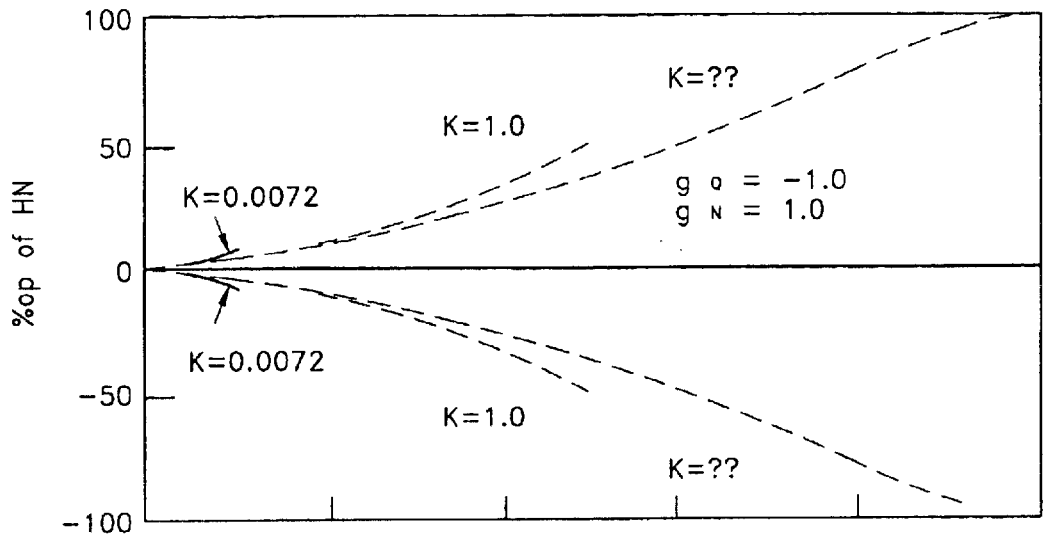
FIG. 3(a) and FIG. 3(b) show the calculated relationship between the optical purity (% op) of the starting material (HQ) or the product (HN), conversion ratio and K, in the reaction system of class (B).
Figure 3B:
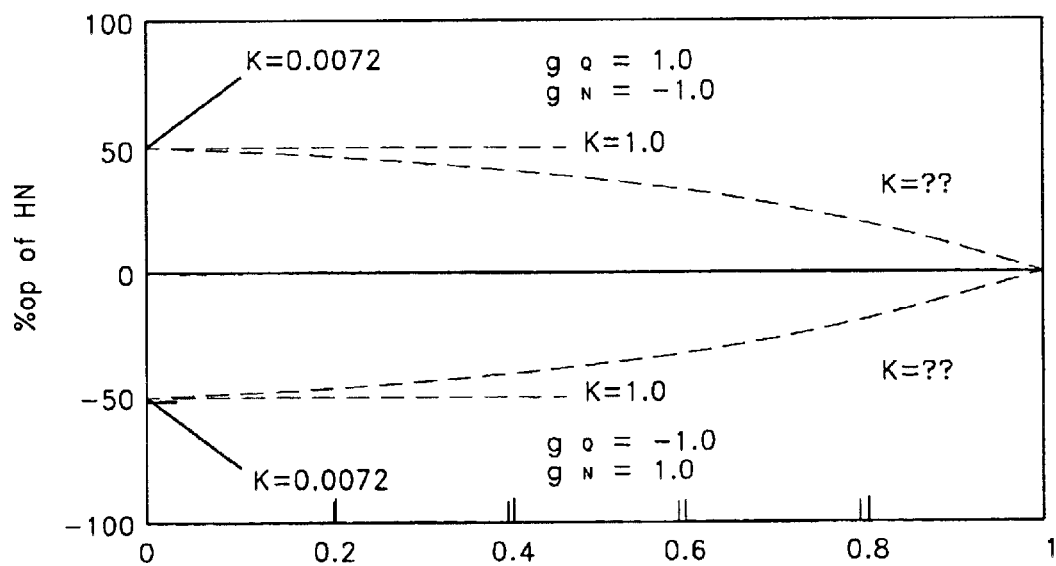

FIG. 3(a) and FIG. 3(b) show the relationship between the optical purity (% op) and K value.

FIG. 3(a) and FIG. 3(b) show the results obtained from equations (24), (25) and (26), in the case of $g_Q \cdot g_N < 0$, $g_Q = -1.0$ and $g_N = 1.0$ and the case of $g_Q = 1.0$ and $g_Q = -1.0$.

The following results are indicated. The optical purity (% op) of the starting material (HQ) increases as the reaction progresses. Especially, as K is smaller, the optical purity (% op) increases more sharply.

The optical purity (% op) of the product (HN) increases when K is less than 1. As K becomes larger, the optical purity (% op) gradually decreases. When K=∞, the optical purity (% op) of the product becomes zero at the end of the reaction. The relationship is the same as in the irreversible reaction.

The above results reveal the following:

when K is less than 1, the optical purity of the product increases as the conversion is increased. In class (A), the optical purity (% op) of the product does not increase beyond the value achieved at the initial stage of reaction, i.e., (g/2)×100%. In contrast, the optical purity (% op) obtained by the reaction in class (B) increases far beyond this value.

As described above, the first embodiment of the invention enables concentration of one starting material enantiomer or diastereomer and one product enantiomer or diastereomer (or achieving further concentration of one starting material enantiomer or diastereomer and one product enantiomer or diastereomer, if already concentrated). According to the second embodiment of the invention, in a reaction system of class (A), one starting material enantiomer and one product enantiomer are concentrated by controlling the g of the starting material. According to the third embodiment of the invention, in a reaction system of class (B), one starting material enantiomer and one product enantiomer are concentrated by controlling at least one of the following:

g's of the starting material and product;

signs of the g's; and

K indicating the photochemical equilibrium of the reaction.

The present invention will be described below in further detail with reference to Examples.

EXAMPLES

Example 1

Absolute asymmetric synthesis was conducted in the reaction system which contains methyl bicyclo[2.2.1]hepta-2,5-diene-2-carboxylate (HN) represented by the formula below and methyl tetracyclo[3.2.0.0$^{2.7}$.0$^{4.6}$]heptane-1-carboxylate (HQ).

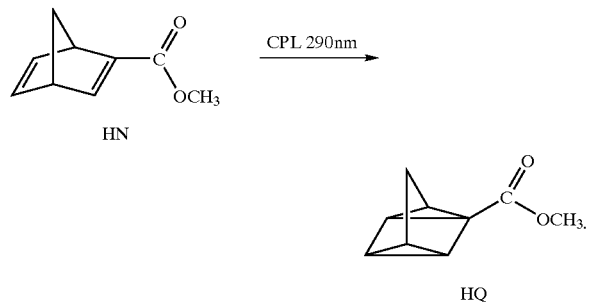

<1> Optical Properties of HN and HQ

HN and HQ were measured for their UV spectra and CD spectra (in CH$_3$CN). The results are shown in FIG. 4(a) to FIG. 4(f) together with the g values derived from these spectra.

The specific rotations (in CH$_3$CN) were (−)-HN: [α]$^{20}_D$=−41.5 (c=0.0624)

(+)-HQ: [α]$^{20}_D$=322 (c=0.00375)

Figures 4A, 4B, 4C, 4D, 4E, 4F:
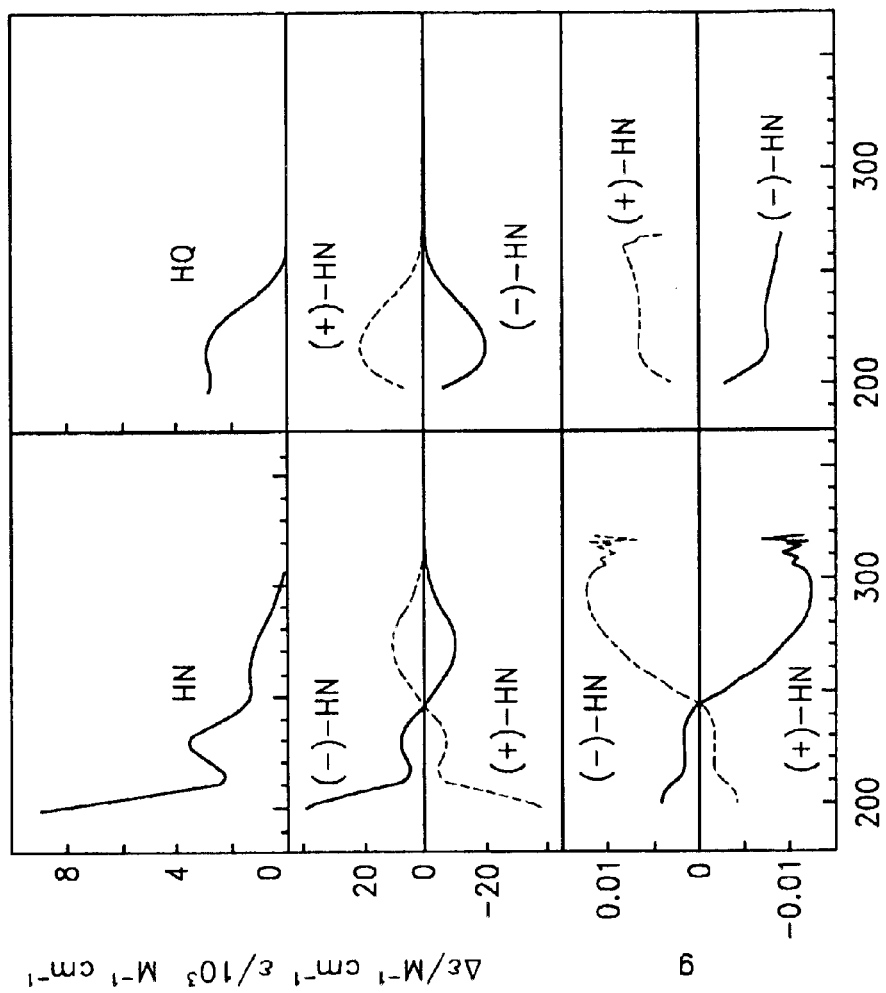
FIG. 4(a) to FIG. 4(f) show optical characteristics of (+)-HN and (−)-HN, and (+)-HQ and (−)-HQ in acetonitrile.

Although norbornadiene and methyl acrylate regarded as model compounds of HN do not have any absorption bands at wavelengths longer than about 250 nm, as is apparent from FIG. 4(a), the UV spectrum of (±)-HN exhibits two absorption maxima at about 229.5 and 265 nm. As shown in FIG. 4(c), (+)-HN and (−)-HN give the CD spectra from 200 to 340 nm. FIG. 4(e) indicates that anisotropic factor g of (+)-HN and (−)-HN also exhibit two maxima in this region.

The foregoing shows that broad absorption of this region consists of two bands.

On the contrary, as shown in FIG. 4(b), the UV spectrum of (±)-HQ exhibits one absorption band composed of an absorption maximum at about 215 nm and an absorption declining toward about 250 nm. This absorption band corresponds to that of methyl acrylate which does not exhibit any absorption at wavelengths longer than 250 nm. As shown in FIG. 4(d), the CD spectra of (+)-HQ and (−)-HQ have the maximum at about 215 nm, and thus absorption bands in the UV and CD spectra appear to be composed of a single band. However, the two maxima of anisotropic factor g at 217.5 and 263.5 nm indicate that the UV and CD spectra of (+)-HQ and (−)-HQ are actually composed of two bands.

<2> Efficiency of Photocyclization and Stereochemistry

The efficiency and stereochemical aspect of the photocyclization of HN into HQ were evaluated by irradiating (−)-HN with a linearly polarized light (LPL) at a wavelength of 290 nm, which is not absorbed by HQ.

Figure 5A:
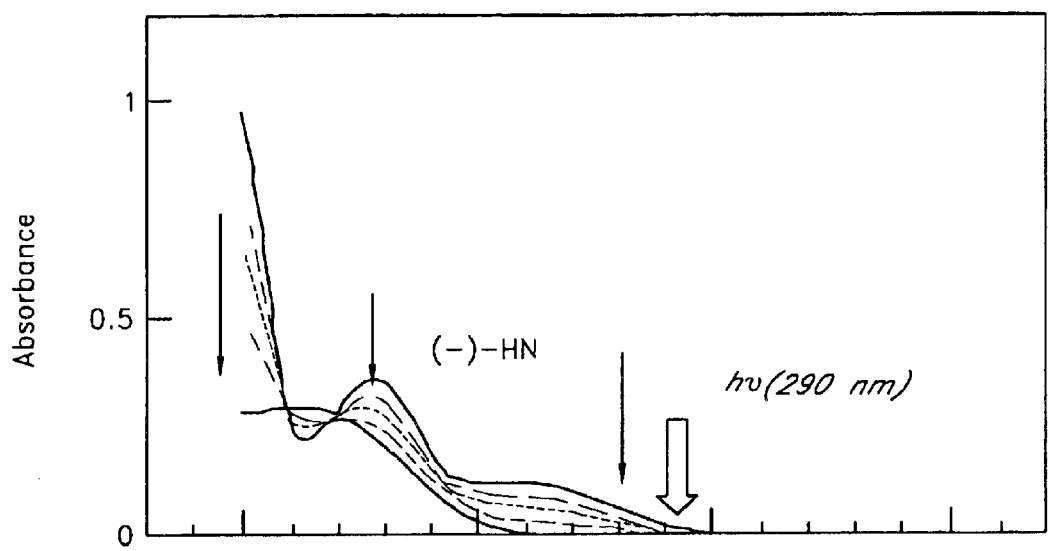
FIG. 5(a) and FIG. 5(b) show UV and CD spectral changes by irradiation of (−)-HN (0.102 mM) in acetonitrile at 290 nm with LPL.

FIG. 5(a) shows changes in UV spectra of (−)-HN in CH$_3$CN (0.236 mM) irradiated at 290 nm with light. This figure shows spectra at various irradiation times (0, 31, 60 and 127 minutes) and the spectrum of (+)-HQ. The absorption bands of (−)-HN at 228 and 256 nm gradually disappeared, and a new absorption band resembling the UV spectrum of HQ appeared at about 220 nm. Two isosbestic points were found at 209 and 218 nm by the photoirradiation.

The reaction mixture was analyzed by gas chromatography using biphenyl as an internal standard. UV spectrum and gas chromatography revealed that the total concentration of HN and HQ was retained after CPL irradiation and no by-products were present.

These results indicate that the photocyclization progressed quantitatively and no side reactions occurred. The fact that the spectrum of (−)-HN irradiated for 127 minutes closely agrees with that of HQ confirmed that the photoirradiation efficiently causes the one-way isomerization from HN into HQ.

Figure 5B:
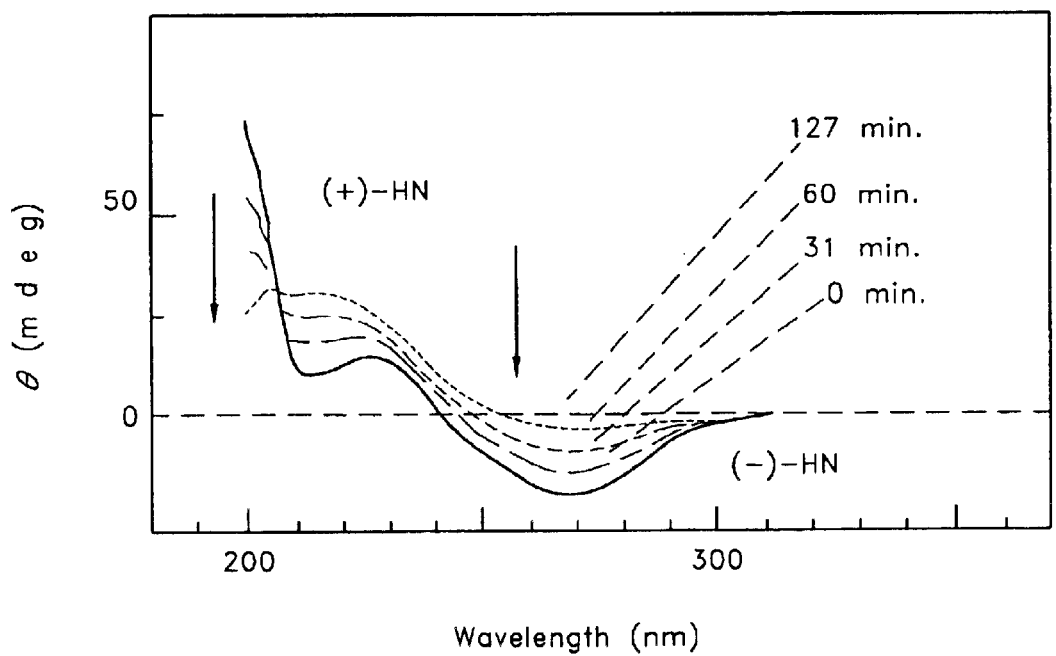

FIG. 5(b) shows changes in CD spectra when (−)-HN was irradiated with 290 nm light. This figure shows the spectra at various irradiation times (0, 31, 60 and 127 min.) and spectrum of (+)-HQ. The absorption maxima of (−)-HN at 229 and 271.5 nm gradually decreased, and a new absorption maximum appeared at about 215 nm. An isosbestic point was observed at 207 nm.

The changes in UV and CD spectra as mentioned above were measured at a wavelength of 290 nm where the product cannot absorb excitation light. The results of the measurement revealed that there was no influence of side reactions or the like. The spectrum of (−)-HN irradiated for 127 minutes corresponds to that of (+)-HQ having the same concentration. This fact confirmed that (−)-HN is isomerized into (+)-HQ without racemization.

<3> Absolute Asymmetric Synthesis with CPL

Absolute asymmetric synthesis was carried out by CPL-irradiating (±)-HN at 290 nm.

Figure 6:
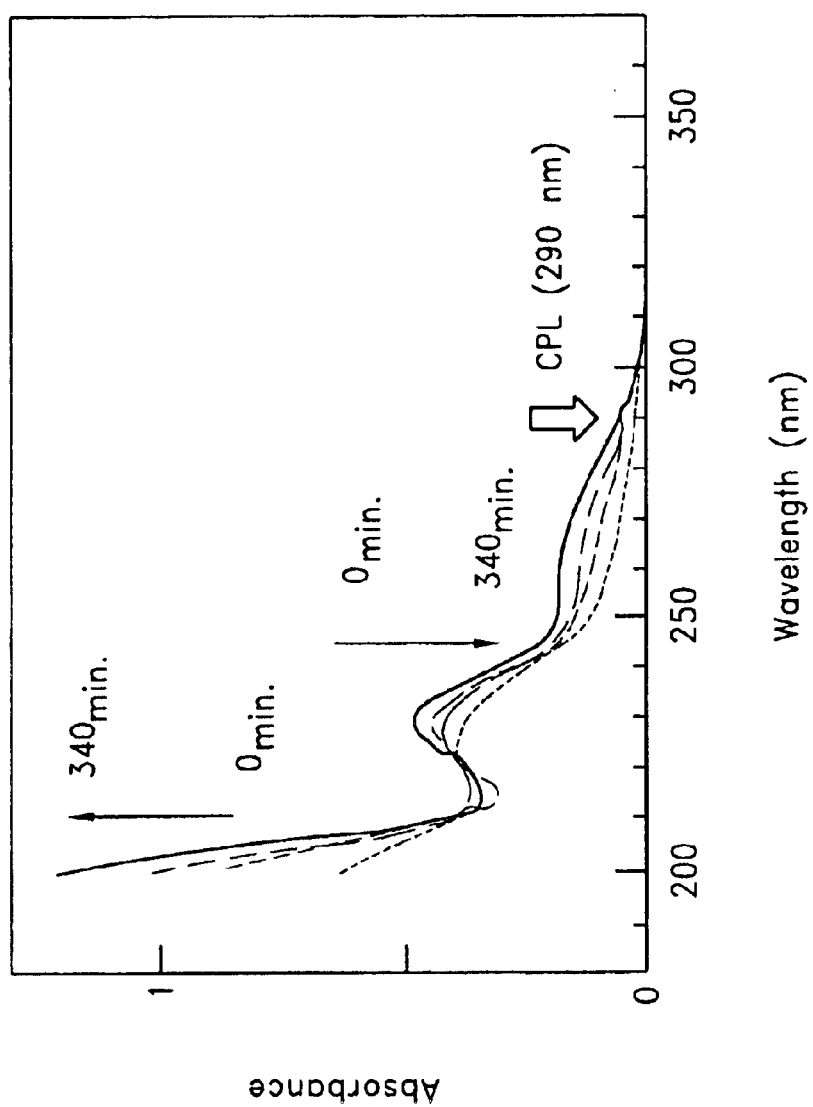
FIG. 6 shows UV spectral changes by irradiation with 290 nm CPL.

FIG. 6 shows changes in UV spectrum over time irradiated at 290 nm with l-CPL.

The intensity of the absorption bands decreased at about 270 nm, and the UV spectrum showed two isosbestic points at 209 and 218 nm. A similar change in the UV spectrum was observed when RN was irradiated at 290 nm with r-CPL or LPL.

Figure 7:
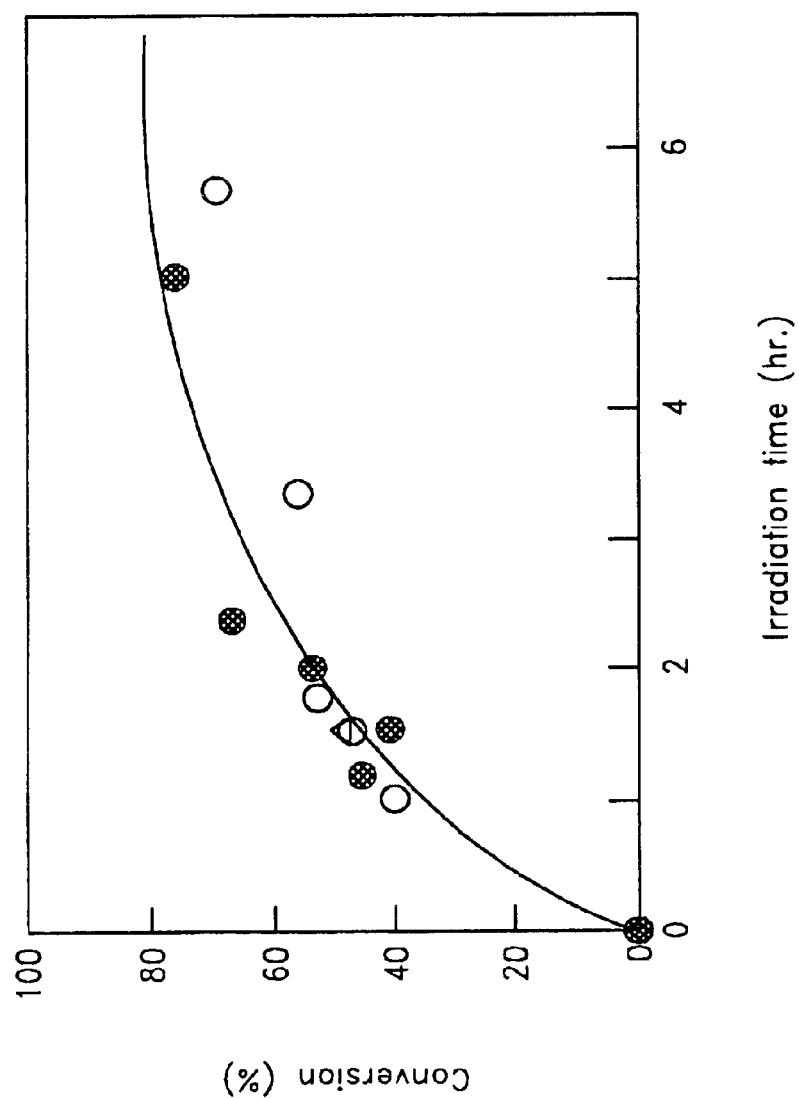
FIG. 7 shows the relationship between irradiation time and the conversion of HN solution irradiated at 290 nm with CPL and LPL.

FIG. 7 shows the relationship between the irradiation time of (±)-HN and conversion when irradiated at 290 nm with r- and l-CPL and LPL. In this figure, white dots represent l-CPL irradiation; black dots represent r-CPL irradiation; and white triangles represent LPL irradiation. Because the plots are overlapping, it is considered that the intensities of the right and left-handed CPL and LPL as incident light are almost equal.

Figure 8A:
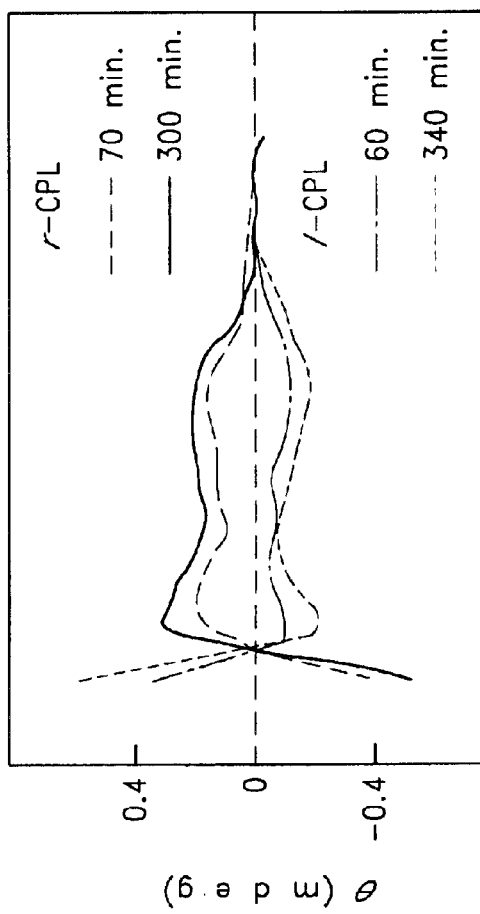
FIG. 8(a) shows CD spectral changes by irradiation of HN acetonitrile solution at 290 nm with l- and r-CPL.

FIG. 8(a) shows changes in CD spectra of HN (acetonitrile solution) when irradiated at 290 nm with l- and r-CPL. The figure indicates that the intensities of the two peaks at about 220 and 280 nm are increasing over time during irradiation.

Figure 8B:
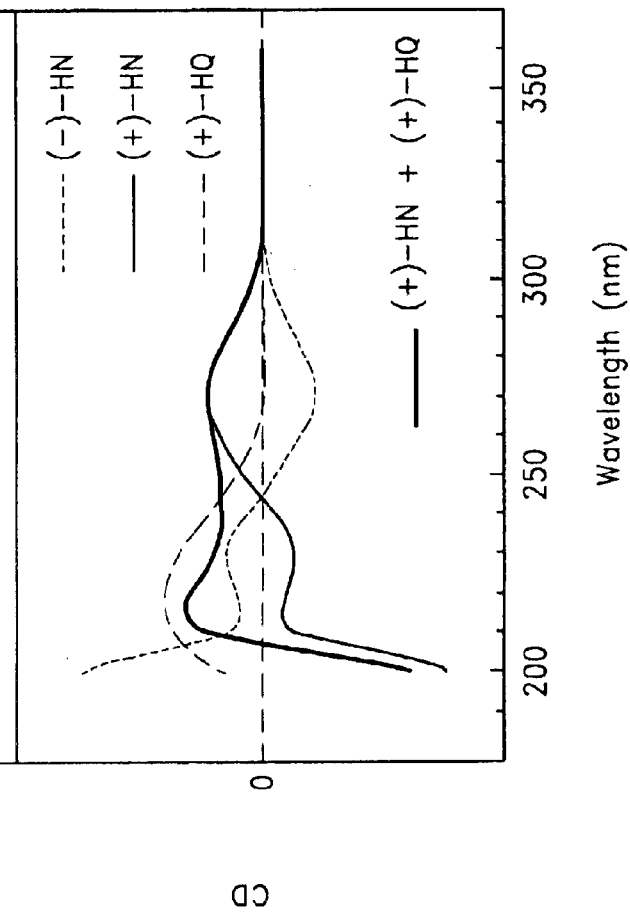
FIG. 8(b) shows calculated CD spectrum of (+)-HN and (−)-HN irradiated with 290 nm r-CPL.

FIG. 8(b) shows the calculated values of the CD spectra of irradiated (±)-HN. It is assumed from this figure that (−)-HN is selectively excited with r-CPL (290 nm) and the concentration of (+)-HN increases.

It is well known that photocyclization is a unimolecular reaction. Thus, a decrease in HN concentration equals to an increase in HQ concentration. When a solution of HN is irradiated at 290 nm with r-CPL, the CD spectrum appears as a 1:1 mix of the CD spectrum of (+)-HN and Δε spectrum of (+)-HQ.

The spectrum shown in FIG. 8(b) was calculated based on the above view. It was confirmed that the spectrum of FIG. 8(a) obtained experimentally precisely agreed with the calculated spectrum of FIG. 8(b).

The CD absorption band at about 280 nm shown in FIG. 8(a) reflects the concentration of one of enantiomers of HN. The value of Δε of (±)-HQ at 280 nm is 0. Thus the optical purity of HN can be determined from the value of ellipticity (θ) at 280 nm. The absorption band at about 220 nm reflects the concentration of one of enantiomers of HQ. In particular, because the value of Δε of (±)-HN at 245 nm is 0, the optical purity of HQ can be determined using the value of θ at this wavelength.

Figures 9A, 9B:
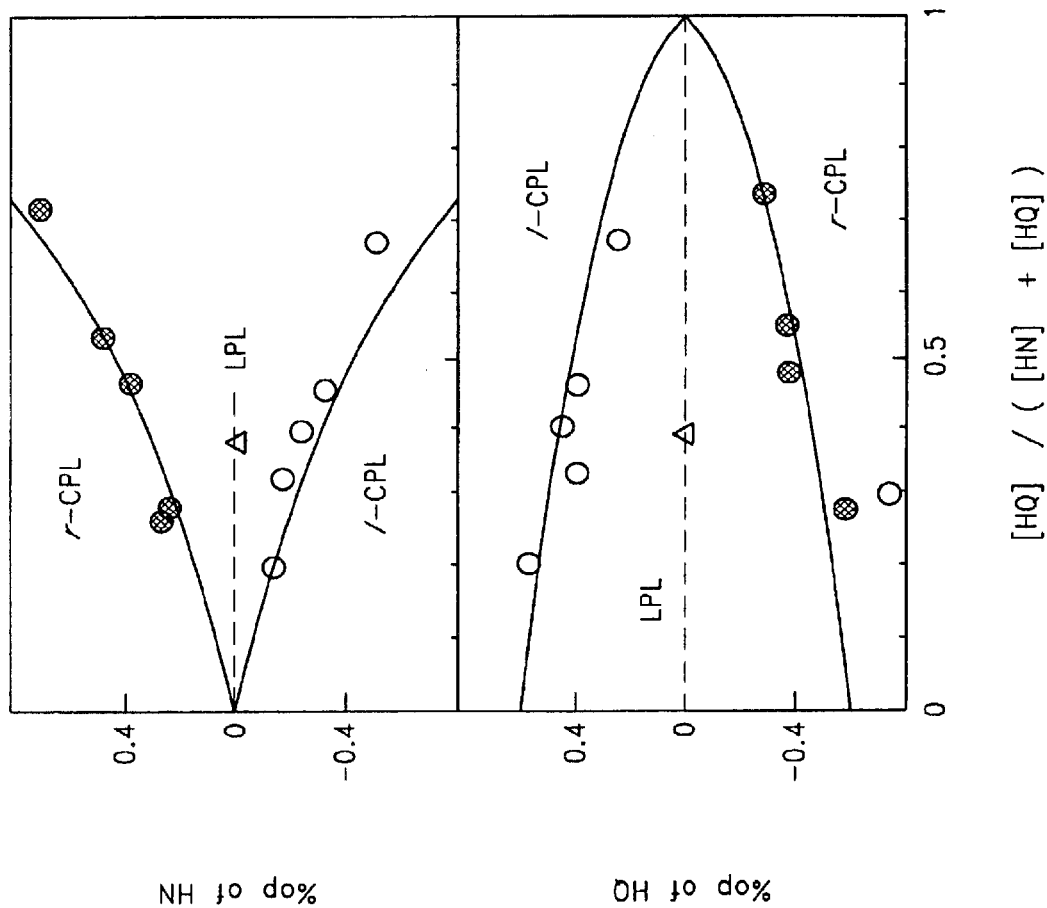
FIG. 9(a) shows the relationship between the optical purity (% op) of the starting material (HN) and conversion ratio.
FIG. 9(b) shows the relationship between the optical purity (% op) of the product (HQ) and conversion.

FIG. 9(a) shows the relationship between the conversion and the optical purity (% op) of HN calculated from the concentration determined by the measurement of CD and UV spectra.

FIG. 9(b) shows the relationship between the optical purity (% op) of HQ and the conversion. In FIGS. 9(a) and (b), black dots represent the results of r-CPL irradiation and white dots represent the results of l-CPL irradiation.

FIG. 9(a) indicates that the optical purity (% op) of HN increases as the conversion ratio increases.

The solid lines in FIGS. 9(a) and (b) are theoretically depicted with Kagan's equation (equation (2) described above) using the measurement of g value (g=0.012) at 290 nm. The curves of solid lines show good agreement with the experimental data.

Therefore, it was confirmed that ( )-HN irradiated with r- and l-CPL at 290 nm increased concentrations of (+)-HN and (−)-HN, and the behavior of % op agreed with equation (2) described above.

Example 2

Absolute asymmetric synthesis was carried out as a photochemical reaction represented by the following formula.

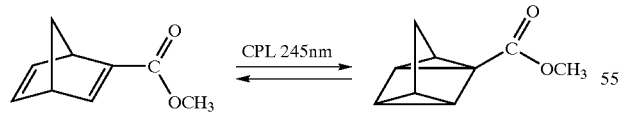

As shown in FIGS. 4(e) and (f) mentioned above, when HQ is irradiated at 245 nm with CPL, one of the enantiomers is selectively excited. However, the g's of (+)-HN and (−)-HN at 245 nm are 0. This means that the selection is not effective in excitation of HN.

Therefore, irradiation of HQ with CPL at the wavelength of 245 nm is discussed.

Figure 10:
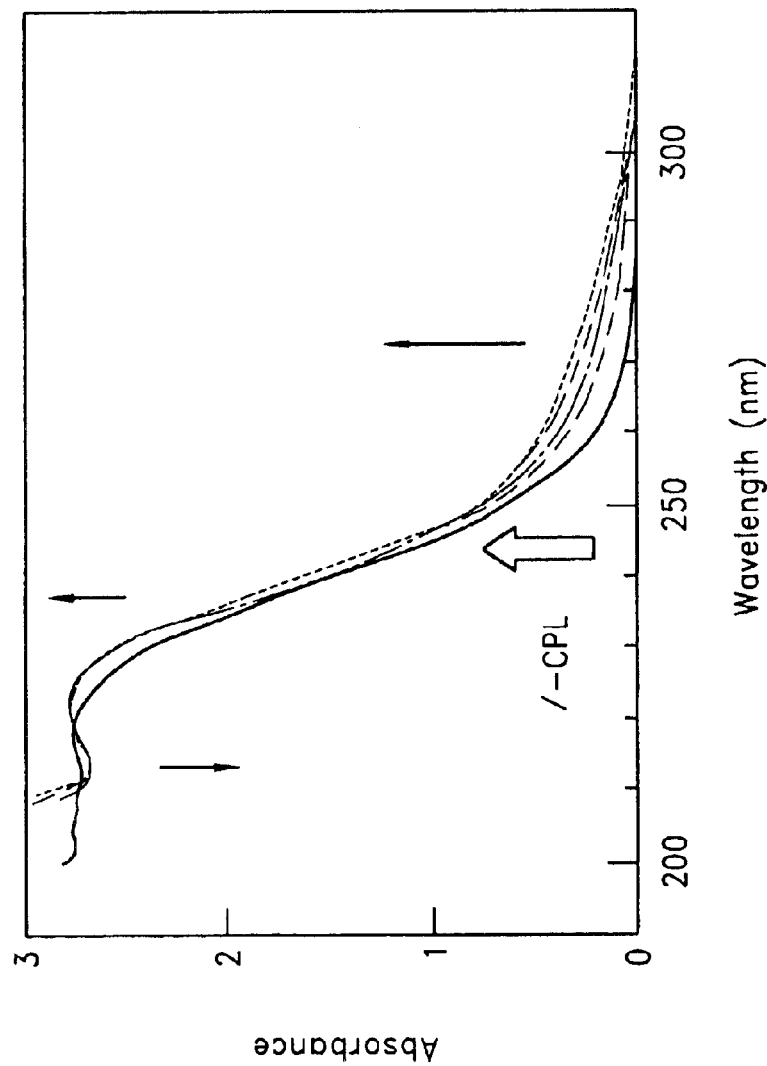
FIG. 10 shows UV spectral changes in HQ solution irradiated at 245 nm with l-CPL.

FIG. 10 shows the measurements of changes in UV spectra of HQ solution irradiated at 245 nm with l-CPL. The absorption intensity was increased at about 270 nm by l-CPL photoirradiation at 245 nm, and the UV spectra show two isosbestic points at 208 nm and 212 nm.

Similar changes in UV spectrum of the HQ solution were observed when irradiated at 245 nm with r-CPL or LPL.

The solution was analyzed by gas chromatography using biphenyl as an internal standard. The gas chromatography chart did not show any signals other than HQ and HN, confirming that the total amount of HQ and HN is maintained.

The appearance of the two isosbestic points of UV spectra and the results of gas chromatography analysis of the solution indicate that HQ is photochemically isomerized into HN without any side reactions. Thus, since HQ is isomerized into HN by photoirradiation at 245 nm, the conversion of HQ into HN is measured by the intensity of UV absorption at 280 nm, which reflects the concentration of the product HN.

Figure 11:
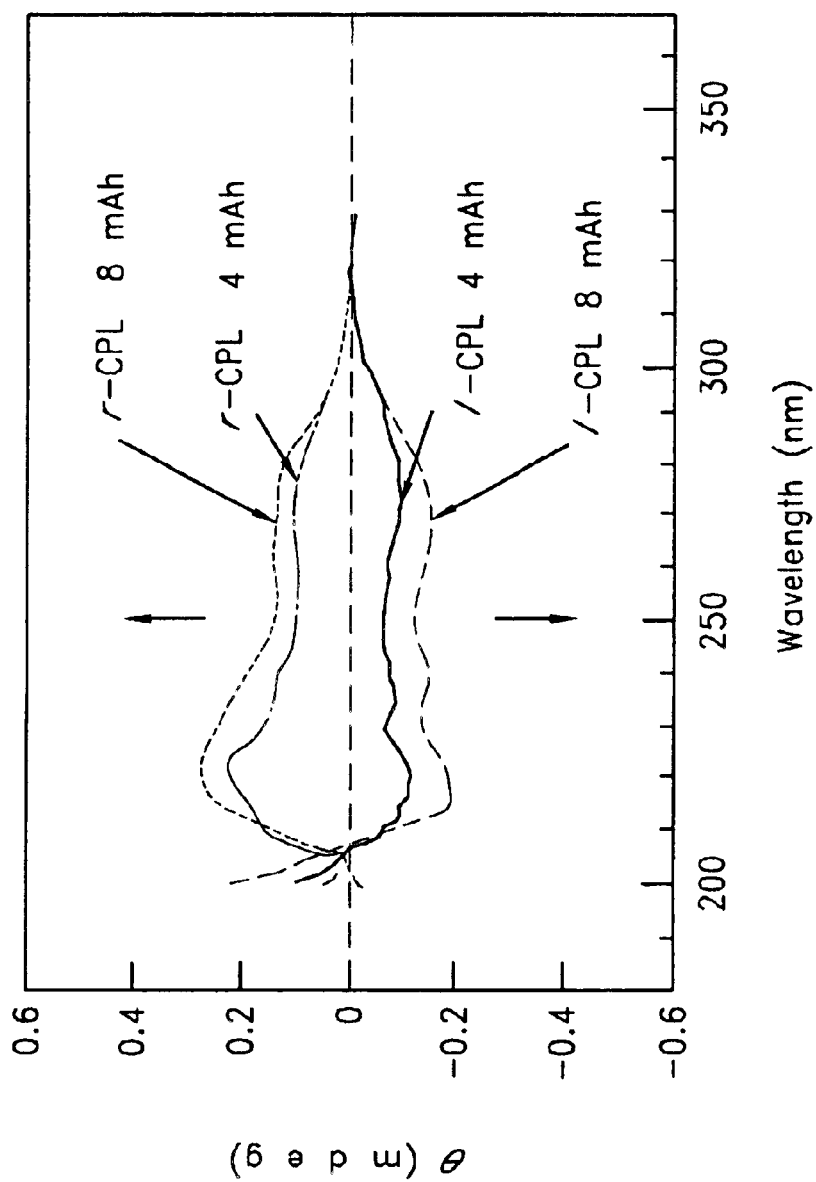
FIG. 11 shows CD spectral changes in HN solution irradiated at 245 nm with l-CPL and r-CPL, respectively. The CD spectra were measured after dilution to 0.29 mM ($[HQ]_0$=0.87 mM).

FIG. 11 shows the measurements of changes in CD spectra of HQ solution irradiated with l-CPL or r-CPL at 245 nm.

Two absorption maxima are observed at about 215 nm and 270 nm, and their intensities increase over time due to CPL photoirradiation.

Figure 12:
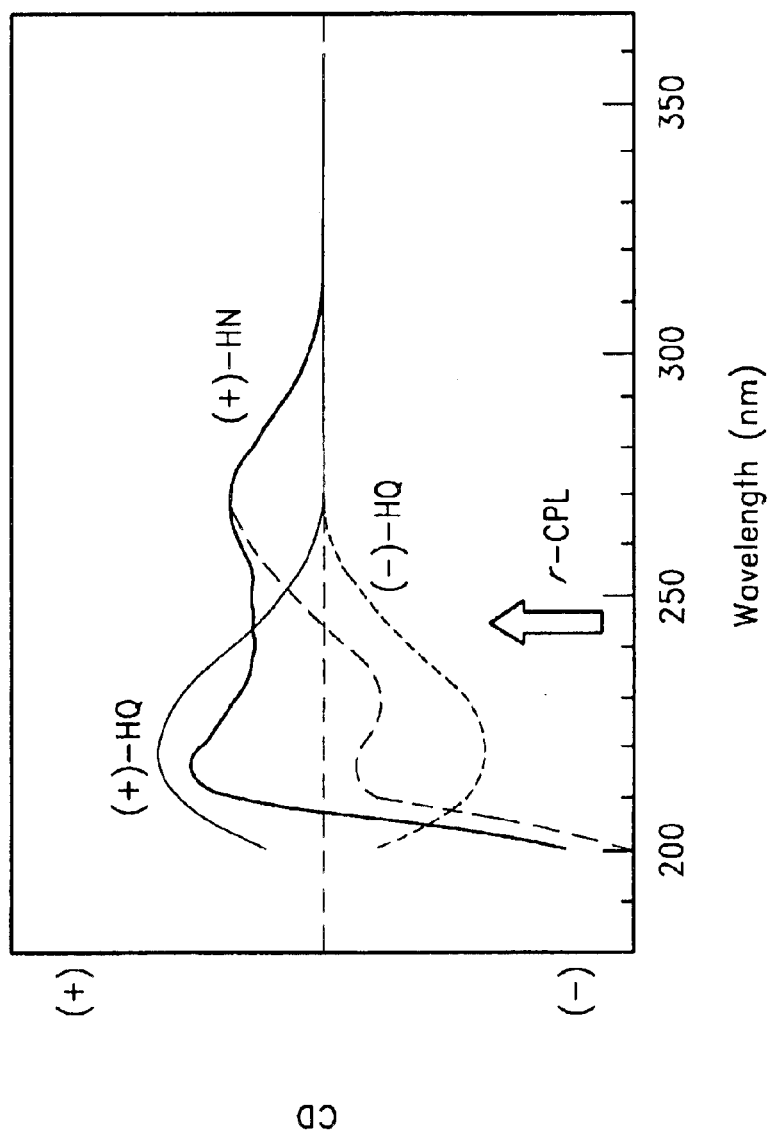
FIG. 12 shows a simulated calculation of CD spectral changes in HQ irradiated at 245 nm with r-CPL.

FIG. 12 shows calculation results of CD spectra of HQ solution irradiated at 245 nm with r-CPL. When the HQ solution is irradiated at 245 nm with r-CPL, (−)-HQ is preferentially excited, whereby (+)-HQ remains and (+)-HN is isomerized into (−)-HQ. Therefore, (−)-HQ excited with r-CPL is isomerized into (+)-HN. This isomerization does not cause any side reactions. In addition, photoisomerization is known to be a unimolecular reaction. Therefore, the CD spectra of the HQ solution when irradiated at 245 nm with r-CPL is composed of the CD spectrum of (+)-HQ and CD spectrum of (+)-HN, and their composition ratio of 1:1 at the initial stage. After continuing photoisomerization, the value of ε of HN is higher than that of HQ at about 245 nm and HN start to be excited by CPL irradiation. Therefore, CD absorption at about 215 nm is higher than that at about 270 nm. In either case, the actual CD spectrum of the HQ solution irradiated at 245 nm with l-CPL is assumed to be similar to the thicker solid line in FIG. 12.

When the HQ solution is irradiated at 245 nm with l-CPL in the same manner, its CD spectra is composed of the CD spectrum of (−)-HQ and CD spectrum of (−)-HN and the calculated shape of CD spectra resemble that shown in FIG. 12.

Accordingly, the above simulation shows that the change at about 280 nm in CD spectrum during the isomerization of HQ irradiated with 245 nm CPL reflects a change in HN concentration, and the change at about 220 nm reflects a change in HN concentration caused by the isomerization of HQ irradiated at 245 nm with CPL.

Since (+)-HQ and (−)-HQ do not have any CD absorption at 280 nm, the optical purities of (+)-HN and (−)-HN are determined by the ellipticities (θ) at 280 nm. Because ΔE of (+)-HN and (−)-HN are 0 at 245 nm, the optical purities of (+)-HQ and (−)-HQ are determined by the ellipticities (θ) at 245 nm.

Therefore, HQ solution is irradiated with 245 nm CPL to cause absolute asymmetric flat synthesis. FIG. 13(a) and FIG. 13(b) show the relationship between the optical purity (% op) and conversion ratio which is obtained as an experimental result. In this figure, the black dots represent the results of r-CPL irradiation; the white dots represent the results of l-CPL irradiation; and the solid line represents the value calculated by simulation in which $g_Q=\pm0.0074$, $g_N=0$ and $K=0.667$.

As is apparent from FIG. 13(a) and FIG. 13(b), the results of experiment and simulation show good agreement. Thus, the optical purity (% op) of HQ increases and the optical purity (% op) of HN decreases as conversion ratio increases. In the photostationary state, the optical purity (% op) of HQ reaches a maximum and the optical purity (% op) of HN becomes minimal.

Next, concerning reversible photoisomerization of HN into HQ caused by 245 nm CPL irradiation, the relationship between the conversion ratio and the optical purities (% op) of the starting material and the product was analyzed.

Changes in the UV spectra of HN solution under irradiation of 245 nm CPL closely resembled those shown in Example 1. Photoirradiation with 245 nm CPL further weakened the absorption at about 270 nm, and the UV spectra exhibited two isosbestic points at about 208 nm and about 212 nm.

These results indicate that no side reactions occur in this photoreaction. Thus, conversion ratio from HN into HQ was determined by the intensity of UV absorption at 280 nm.

Changes in CD spectra closely resembled those shown in FIG. 11. Therefore, the optical purities of (+)-HN and (−)-HN were determined by the ellipticities at 280 nm, and the optical purities of (+)-HQ and (−)-HQ were determined by the ellipticities at 245 nm.

Because the g of HN is 0 at 245 nm, enantiomers are not concentrated by CPL irradiation at the initial stage of photoisomerization from HN into HQ. However, CPL serves as an asymmetric source for HQ produced by photoisomerization of RN. As the conversion ratio from HN into HQ increases, the produced HQ is excited by CPL and the concentration of one enantiomer of HQ progresses. Accordingly, the concentration of one enantiomer of HN also progresses.

FIGS. 14(a) and (b) show the relationship between the optical purity (% op) and conversion ratio as experimental data (black dots: r-CPL irradiation, white dots: l-CPL irradiation) and simulated calculation results (solid line) of HN in acetonitrile irradiated at 245 mm with CPL. The simulated calculation results are when $g_N=0$, $g_Q=\pm0.0074$ and $K=1.5$. The experimental results and calculated results showed good agreement. The optical purities (% op) of HN and HQ increase as conversion ratio increases. In the photostationary state, the values of these optical purities (% op) were almost equal.

The above results show that the aforementioned reaction system of class (B) in absolute asymmetric synthesis is formed.

Further, the results of theoretical and experimental analyses reveal the following: the concentration of one of the enantiomers in the starting material and one of the enantiomers in the product can be controlled by adjusting the g's of both staring material and product, the plus or minus sign of the g's and the K, which represent photochemical equilibrium of the reaction;

the optical purities (% op) of the starting material and product increase as the conversion ratio increases when the g's of the starting material and product are sufficiently high, the signs of the g of the starting material is opposite to that of the product, and K is not 1;

and the optical purities of the staring material and product increase to a considerable extent in the photostationary state. This indicates that Kagan's assumption that the purity of enantiomers of the product decreases by the process of photoreaction is not always the case in the absolute asymmetric synthesis of class (B). The above Examples reveal that one of the enantiomers in the starting material and one of the enantiomers in the product can be concentrated by the progress of photoreaction using CPL irradiation.

INDUSTRIAL APPLICABILITY

As described above in detail, the present invention provides a novel method for absolute asymmetric synthesis comprising irradiating the reaction system with circularly polarized light, the method enabling concentration of one of the enantiomers in the starting material and one of the enantiomers in the product.

What is claimed is:

1. A method for synthesizing absolute asymmetry which comprises:

providing a photochemically reversible reaction system in which a starting material and product are each mixtures of enantiomers or diastereomers not photochemically or thermally converted into each other; and irradiating the reaction system with right- or left-circularly polarized light to excite the starting material alone or both of the starting material and the product, thereby concentrating one of the enantiomers or diastereomers in the starting material and one of the enantiomers or diastereomers in the product that corresponds to the enantiomer or diastereomer not concentrated in the starting material.

2. The method according to claim 1 wherein the starting material and the product are mixtures of enantiomers and only the starting material is excited, the concentration of one of the enantiomers in the starting material and one of the enantiomers in the product being controlled by adjusting the anisotropic factor g which indicates the degree of selective excitation by the right- or left-circularly polarized light.

3. The method according to claim 1 wherein the starting material and the product are mixtures of enantiomers and both of the starting material and the product are excited, the concentration of one of the enantiomers in the starting material and one of the enantiomers in the product being controlled by adjusting at least one of the following:

the value of anisotropic factor g which indicates the degree of selective excitation by the right- or left-circularly polarized light;

plus or minus sign of g; and

K indicating the photochemical equilibrium of the reaction.

4. The method according to claim 1 wherein the starting material is a norbornadiene derivative and the product is a quadricyclane derivative.

5. A method for synthesizing absolute asymmetry which comprises:

providing a photochemically reversible reaction system in which a starting material and its isomerized product are each mixtures of enantiomers or diastereomers not photochemically or thermally converted into each other; and increasing a concentration of one of the enantiomers or diastereomers in the starting material and simultaneously increasing a concentration of one of the enantiomers or diastereomers in the product that corresponds to the enantiomer or diastereomer not concentrated in the starting material, by irradiating the reaction system with right- or left-circularly polarized light to excite and isomerize the starting material alone or both of the starting material and the product.

6. The method according to claim 5, wherein the starting material and the product are mixtures of enantiomers and only the starting material is excited and isomerized, and wherein the one of the enantiomers in the starting material and the one of the enantiomers in the product are concentrated as a function of the anisotropic factor g which indicates the degree of selective excitation by the right- or left-circularly polarized light.

7. The method according to claim 5, wherein the starting material and the product are mixtures of enantiomers and both of the starting material and the product are excited and isomerized, and wherein the one of the enantiomers in the starting material and the one of the enantiomers in the product are concentrated as a function of at least one of the following:

the value of anisotropic factor g which indicates the degree of selective excitation by the right- or left-circularly polarized light;

plus or minus sign of g; and

K indicating the photochemical equilibrium of the reaction.

8. The method according to claim 5, wherein the starting material is a norbomadiene derivative and the product is a quadricyclane derivative.

9. The method according to claim 8, wherein the right- or left-circularly polarized light has a frequency of 290 nm.

10. The method according to claim 5, wherein the starting material is a quadricyclane derivative and the product is a norbomadiene derivative.

11. The method according to claim 9, wherein the right- or left-circularly polarized light has a frequency of 245 nm.

* * * * *